(12) United States Patent
Pryor et al.

(10) Patent No.: US 6,296,937 B2
(45) Date of Patent: Oct. 2, 2001

(54) SILICA ADSORBENT ON MAGNETIC SUBSTRATE

(75) Inventors: James Neil Pryor, West Friendship; Linda Lee Crump, Crownsville, both of MD (US)

(73) Assignee: W. R. Grace & Co.-Conn., Columbia, MD (US)

( * ) Notice: Subject to any disclaimer, the term of this patent is extended or adjusted under 35 U.S.C. 154(b) by 0 days.

(21) Appl. No.: 09/756,149

(22) Filed: Jan. 8, 2001

Related U.S. Application Data

(63) Continuation of application No. 08/786,600, filed on Jan. 21, 1997.

(51) Int. Cl.$^7$ .................................................... B32B 5/16
(52) U.S. Cl. ........................................... 428/403; 428/404
(58) Field of Search ..................................... 428/403, 404

(56) References Cited

U.S. PATENT DOCUMENTS

| | | | |
|---|---|---|---|
| 2,885,366 | 5/1959 | Iler | 252/313 |
| 2,913,419 | 11/1959 | Alexander | 252/313 |
| 4,082,905 | 4/1978 | Stephan et al. | 428/538 |
| 4,233,169 | 11/1980 | Beall et al. | 252/62.59 |
| 4,280,918 | 7/1981 | Homola et al. | 252/62.51 |
| 4,297,337 | 10/1981 | Mansfield et al. | 424/1 |
| 4,309,459 | 1/1982 | Tokuoka | 427/219 |
| 4,336,310 | 6/1982 | Okuyama et al. | 428/447 |
| 4,554,088 | 11/1985 | Whitehead et al. | 252/62.54 |
| 4,564,537 | 1/1986 | Austin et al. | 427/376.4 |
| 4,628,037 | 12/1986 | Chagnon et al. | 436/526 |
| 4,695,392 | 9/1987 | Whitehead et al. | 252/62.54 |
| 4,695,393 | 9/1987 | Whitehead et al. | 252/62.54 |
| 4,698,302 | 10/1987 | Whitehead et al. | 435/94 |
| 4,804,561 | 2/1989 | Tanioka et al. | 427/130 |
| 5,039,559 | 8/1991 | Sang et al. | 427/213.3 |
| 5,055,194 | 10/1991 | Goetz et al. | 210/635 |
| 5,217,804 | 6/1993 | James et al. | 428/329 |
| 5,236,623 | 8/1993 | Chevallier | 516/82 |
| 5,279,936 | 1/1994 | Vorpahl | 435/6 |
| 5,316,699 | 5/1994 | Ritter et al. | 252/584 |
| 5,340,393 | 8/1994 | Jacobson | 106/492 |
| 5,368,933 | 11/1994 | Aoki et al. | 428/329 |
| 5,389,482 | 2/1995 | Okano et al. | 430/106.6 |
| 5,470,660 | 11/1995 | Misawa et al. | 428/403 |
| 5,512,332 | 4/1996 | Liberti et al. | 427/550 |
| 5,512,405 | 4/1996 | Misawa et al. | 430/106.6 |
| 5,578,238 | 11/1996 | Weiss et al. | 252/62.52 |
| 5,597,531 | 1/1997 | Liberti et al. | 422/57 |
| 5,610,274 | 3/1997 | Wong | 530/334 |
| 5,662,824 | 9/1997 | Sang et al. | 252/62.56 |
| 5,683,875 | 11/1997 | Lichtenwalter | 435/6 |
| 5,698,271 | 12/1997 | Liberti et al. | 427/550 |
| 5,705,137 | 1/1998 | Goerl et al. | 423/335 |
| 5,734,020 | 3/1998 | Wong | 530/350 |
| 6,027,945 | 2/2000 | Smith et al. | 436/526 |

FOREIGN PATENT DOCUMENTS

| | | | |
|---|---|---|---|
| 4307262 | 9/1994 | (DE) | C09K/3/00 |
| 125 995 | 11/1991 | (EP) | G01N/33/553 |
| 652 490 | 5/1995 | (EP) | G03G/9/083 |
| 757 106 | 5/1997 | (EP) | C12Q/1/68 |
| 5281778 | 10/1993 | (JP) | G03G/9/08 |
| 7235407 | 9/1995 | (JP) | H01F/1/00 |
| WO 91/02811 | 3/1991 | (WO) | C12Q/1/10 |
| WO 93/10162 | 5/1993 | (WO) | C08F/283/00 |
| WO 95/06652 | 3/1995 | (WO) | C07H/1/06 |
| WO 96/03653 | 2/1996 | (WO) | G01N/33/543 |
| WO 96/11054 | 4/1996 | (WO) | B01J/13/04 |

*Primary Examiner*—Hoa T. Le
(74) *Attorney, Agent, or Firm*—Charles A. Cross

(57) ABSTRACT

Adsorbent particles comprising superparamagnetic and/or low Curie Temperature transition metal-containing cores surrounded by a hydrous siliceous oxide coating can be formed by an aqueous process wherein the core is precipitated from an aqueous solution and a siliceous oxide coating is deposited thereon while complete drying of the core is avoided until after the siliceous oxide is deposited. The resulting siliceous adsorbents exhibit strong superparamagnetic and/or low Curie temperature magnetic properties with low transition metal leachability.

20 Claims, No Drawings

US 6,296,937 B2

SILICA ADSORBENT ON MAGNETIC SUBSTRATE

CROSS-REFERENCE TO RELATED APPLICATIONS

This is a continuation of application Ser. No. 08/786,600, filed Jan. 21, 1997.

Reference is made to concurrently filed U.S. patent application Ser. No. 08/785,097, now U.S. Pat. No. 6,027,945, entitled "Methods of Isolating Biological Target Materials Using Silica Magnetic Particles", the disclosure of which is incorporated herein by reference.

BACKGROUND OF THE INVENTION

Adsorbent materials having magnetic properties are known. Often magnetic properties such as ferromagnetism and superparamagnetism are desired to enable use of magnetic fields in various processes. Superparamagnetism is of special interest in many chemical applications where it is desired to collect and redisperse adsorbent particles. The particles of the prior art generally comprise a superparamagnetic material (e.g. magnetite) which is enveloped in or treated with some diverse material.

For many applications, the materials of the prior art have been considered adequate, however for certain applications, the materials of the prior art are inadequate due to their vulnerability to leaching in acidic environments or their lack of sufficient magnetic performance. In many applications such as processing of edible substances or sensitive biological materials (e.g. nucleic acid purification such as described in published patent application W095/06652), these deficiencies result in poor performance or simply prohibit use of these materials.

Thus, there is a need for improved coated superparamagnetic particles, especially particles useful as superparamagnetic adsorbents. Further, there is a need for improved methods of making such adsorbents.

SUMMARY OF THE INVENTION

The invention provides improved siliceous oxide-coated magnetic particles having a high resistance to leaching of the magnetic material on exposure to aqueous acidic environments while also possessing a hydrous siliceous oxide adsorptive surface and excellent magnetic response.

In one aspect, the invention encompasses particles having a superparamagnetic or low Curie Temperature core surrounded by a hydrous siliceous oxide coating wherein the particles exhibit little or no transition metal leaching on exposure to acidic media. The particles preferably exhibit low metal leaching even after sonication (i.e. ultrasonic treatment).

In another aspect, the invention encompasses methods for forming siliceous coatings on superparamagnetic or low Curie Temperature cores wherein the method comprises forming an aqueous dispersion of the cores and depositing a siliceous oxide coating on said dispersed cores wherein said deposition process has an end pH of about 9 or less. Preferably, the aqueous dispersion of the cores is achieved by precipitation of the cores (crystals) in an aqueous medium and maintaining the cores in contact with an aqueous medium from the moment of their precipitation through the deposition of the silica coating thereon.

In another aspect, the invention encompasses methods for adsorbing substances wherein particles having a superparamagnetic or low Curie Temperature core surrounded by a hydrous siliceous oxide coating are used to adsorb a substance from a system and the adsorbent is subsequently removed from the system by application of a magnetic field.

The core material is preferably a superparamagnetic material such as magnetite.

DETAILED DESCRIPTION OF THE INVENTION

The invention provides improved particles comprising siliceous oxide-coated superparamagnetic or low Curie Temperature cores having a high resistance to leaching of transition metal on exposure to aqueous acidic environments while also possessing a hydrous siliceous oxide adsorptive surface (i.e. a surface characterized by the presence of silanol groups) and excellent magnetic response. The particles of the invention may comprise agglomerates of these siliceous oxide-coated cores.

The particles of the invention are especially characterized by their (1) high resistance to leaching of metal from the magnetic core, especially on exposure to acidic environments, (2) excellent magnetic performance (e.g. their ability to be separated from a liquid by application of a magnetic field and their dispersibility in the absence of a magnetic field), and (3) excellent adsorption/desorption behavior, especially for adsorption/desorption of genetic biological material from a lysate.

For the purpose of describing this invention, the "core" refers to all the material which is surrounded by the siliceous oxide coating. The core of the particles of the invention may be any material which is amenable to the silica coating process which material exhibits superparamagnetic performance (including materials which exhibit a relatively low remanent magnetism) and/or has a low Curie Temperature. Preferably, the core comprises a superparamagnetic material having a remanent magnetism of less than about 10 emu/g, more preferably less than about 2 emu/g, most preferably 0 to 1 emu/g. Where a low Curie Temperature magnetic material is used, that material preferably has a Curie Temperature below about 100° C., more preferably between about -50° C. and 100° C., most preferably between about 0° C. and 90° C. The core materials are generally characterized by the presence of one or more transition metals. Of the superparamagnetic materials, metal oxides containing group VIII transition metal are preferred, magnetite iron oxide being most preferred. The core preferably consists essentially of iron magnetite.

In general, superparamagnetic materials are preferred over low Curie Temperature magnetic materials since they do not require a change in temperature to cause loss of magnetism on removal of an external field. Particles of the superparamagnetic materials may be easily redispersed on removal of any external magnetic field due to their low or non-existent remanent magnetism whereas the low Curie Temperature materials require elevation of the temperature to a level above the Curie Temperature to permit easy redispersion of the particles on removal of any external magnetic field.

The magnetic behavior of many materials often varies with the physical size and state of the material. Thus, materials may exhibit differing magnetic performance depending on their crystal size, their temperature or their physical surroundings (e.g. if they are embedded in a matrix). For magnetite and most other superparamagnetic materials, the material should have a crystal size (diameter) less than about 1000 Å, more preferably about 600 Å or less. In some cases, it may be possible to form the core from a combination of the above-mentioned magnetic materials. Alternatively, it may be possible to dilute the composition of the core with a portion of non-magnetic material depending on the magnetic material used and the desired degree of response to an applied magnetic field. In general, it is preferred that the core consist essentially of superparamagnetic material.

In some instances, it may be possible to form one or more intermediate layers of a diverse non-siliceous oxide material on the surface of the superparamagnetic or low Curie Temperature material. Preferably, intermediate layers of metals such as gold or noble metals are avoided. Most preferably, all intermediate layers are avoided such that the siliceous oxide coating directly contacts the surface of the superparamagnetic or low Curie Temperature material. In some instances, the superparamagnetic or low Curie Temperature material may possess a surface region of slightly higher oxygen content associated with incidental oxidation of the material surface or exposure to mildly oxidizing environments. Such regions of higher oxygen are not considered as intermediate layers for purposes of describing the invention.

The siliceous oxide coating may be of any composition which provides the desired silanol functionality as well as the desired porosity/surface area and barrier properties. In general, the siliceous oxide coating preferably contains at least about 80 wt. % (dry basis) $SiO_2$, more preferably at least about 90 wt. % (dry basis), most preferably 95 to 100 wt. % (dry basis). The siliceous oxide coating preferably does not contain significant amounts of transition metals in a form prone to leaching. In general, the amount of transition metal in the siliceous oxide coating is preferably less than 1 wt. % (dry basis), more preferably less than 0.1 wt. %, most preferably 0–0.01 wt. %. The siliceous oxide coating may contain alkali metal ions associated with the formation of the coating, however, the coating preferably contains less than about 1 wt. % (dry basis) of alkali metal measured as a alkali metal oxide, more preferably less than about 0.5 wt. %, most preferably less than about 0.3 wt. %.

The siliceous oxide coating is characterized by a hydrous surface, that is a surface having silanol groups thereon. If porous, the siliceous oxide may also contain free water in its pores. The pores may be partly or completely filled with water depending on whether the material is dried after the siliceous oxide coating is formed. The siliceous oxide is preferably amorphous.

The siliceous oxide coating preferably is porous. The presence of porosity may have both positive and negative effects on the performance of the material in adsorption and/or desorption depending on the nature of the porosity and the material to be adsorbed and/or desorbed. In cases where both adsorption and subsequent desorption are desired, the pores of the siliceous oxide coating are preferably such that they provide additional surface for adsorption, but do not significantly prevent desorption. In this context, pores of some intermediate size are generally preferred depending on the size of the materials to be adsorbed/desorbed. Such pores will be large enough such that the desired adsorbed species is not excessively inhibited from desorption at a later point in the process. In most circumstances, the external surface of the siliceous oxide coating is also effective to provide adsorption. Thus, accessible internal surface (i.e. porosity) may not be required to achieve a usable product.

In general, the siliceous oxide coated particles preferably have a total pore volume measured by nitrogen BET method of at least about 0.2 ml/g, more preferably about 0.5 to 1.5 ml/g based on the total mass of the particles. Of the total pore volume measured by nitrogen BET, preferably at least about 50% of the pore volume is contained in pores having a diameter of 600 Å or greater, more preferably at least about 60%, most preferably about 70 to 85%. The siliceous oxide coated particles preferably have a nitrogen BET surface area, based on the total mass of the particles, of at least 5 $m^2/g$, more preferably at least about 30 $m^2/g$, most preferably about 40–500 $m^2/g$.

As noted above, the particles of the invention are may comprise an agglomeration of siliceous oxide-coated superparamagnetic or low Curie Temperature crystal cores. The agglomerates themselves may have additional siliceous oxide coating on their accessible surfaces. While the relative amounts of the core material and the siliceous oxide coating may be varied considerably, the particles of the invention preferably comprise at least 30 wt. % of the superparamagnetic or low Curie Temperature core material based on the total particle composition, more preferably at least 50 wt. %, most preferably about 60–80 wt. %. In general, higher amounts of core material will provide stronger response to an applied magnetic field. When the particles are present in a liquid while the magnetic field is applied, the drag characteristics (resistance to particle movement in the fluid associated with the particle-fluid interface and the particle morphology) of the particles themselves will also affect the strength and speed of response (i.e. particle movement) to the applied field.

The particles of the invention may be made in various sizes. Smaller particles provide more surface area (on a weight basis) for adsorption, but they also tend to exhibit a higher amount of drag. The particles of the invention preferably have a median particle size of about 1–15 μm, more preferably about 3–10 μm, most preferably about 4–7 μm. The particle size distribution may also be varied. In general, a relatively narrow monodal particle size distribution is preferred. The particle size distribution is preferably such that about 80 wt. % of the particles are within a 10 μm range about the median particle size, more preferably within an 8 μm range, most preferably within a 6 μm range.

The particles of the invention are generally useful for all applications where siliceous oxide adsorbents are used. Thus, the particles of the invention may be used as selective adsorbents in liquids, as desiccants, odor adsorbents, volatile organic adsorbents, etc. The particles are especially useful for selective adsorption of macromolecular constituents (especially organics) from liquids. The particles are especially useful in mild environments and in highly acidic environments.

In processes involving adsorption from liquids, the particles can be easily dispersed in the liquid in the absence of any applied magnetic field. Once the desired adsorption has taken place, the particles may be removed from the liquid by conventional techniques such as centrifugation or filtration, however, the particles of the invention are especially suited for separation from the liquid by application of a magnetic field across the liquid. A further advantage of the particles of the invention is that they can be easily redispersed on removal of the magnetic field. For low Curie Temperature materials, the application of the magnetic field should take place below the relevant Curie Temperature. On removal of the applied magnetic field, the low Curie Temperature material would have to be heated to a point above the Curie Temperature in order to reduce the remanent magnetism and allow redispersion.

The particles of the invention are preferably further characterized by their performance in these various applications. Specifically, the particles of the invention are preferably characterized by excellent resistance to leaching of metals from the core on exposure of the particles to acidic environments. The particles of the invention are preferably characterized by excellent response to external magnetic fields as demonstrated by the separation rate of the particles on application of a magnetic field to a liquid containing the particles. The particles of the invention are preferably characterized by high adsorption capacity and high desorption release of organic constituents, especially genetic biological materials (e.g. DNA, RNA, etc.).

The metal leaching property of the adsorbent of the invention is measured by placing 0.33 g of the particles (oven dried @ 110° C.) into 20 ml of 1N HCl aqueous solution (using deionized water). The resulting mixture is then agitated only to disperse the particles. After about 15 minutes total contact time, a portion of the liquid from the mixture is then analyzed for metals content. Any conventional elemental analysis technique may be employed, but inductively coupled plasma spectroscopy (ICP) is preferred. By this test, the particles of the invention preferably exhibit a leaching value for transition metals from the core of about 50 ppm or less (solution concentration), more preferably about 10 ppm or less, most preferably about 5 ppm or less. A low leaching value is especially important where the core contains an iron-based material (e.g. magnetite) and the particles are to be used in an application involving recovery, treatment or analysis of biological materials.

The responsiveness of the materials of the invention to an applied magnetic field is determined by measuring the light transmission (or absorption) through a liquid containing the particles upon application of a magnetic field via an external magnet. In order to make this measurement, a standard 1 cm square spectrophotometer curvette (1 cm path length) containing 2 ml deionized water is used as a reference and transmission is measured using a 590 nm wavelength light source. The materials of the invention were tested at 1 wt. % concentration of particles in a 2 ml deionized water sample. For application of the magnetic field, a 1 cm by 1 cm by 0.7 cm rare earth magnet (mass=about 5.8 g) was placed directly under the curvette in the spectrophotometer (preferably a Shimadzu Instruments Model U-1601) such that the magnet was coextensive with the bottom of the curvette. The % transmission of light was then measured at intervals of 40 and 600 seconds. By this test, the particles of the invention preferably give a light transmittance after 40 seconds of at least about 60%, more preferably at least about 75%. The particles of the invention preferably give a light transmittance after 600 seconds of at least 80%, more preferably at least 90%, most preferably at least 95%.

The adsorptive capabilities of the materials of the invention can be characterized in terms of adsorption capacity and desorption yield. The materials of the invention preferably meet or exceed the adsorption/desorption performance described in U.S. patent application Ser. No. 08/785,097, now U.S. Pat. No. 6,027,945, entitled "Methods of Isolating Biological Target Materials Using Silica Magnetic Particles" filed on the same day as the present application.

The particles of the invention may be made by a variety of methods. These methods generally involve the formation of an aqueous slurry of dispersed core particles having the desired magnetic properties and deposition of a siliceous coating onto the surface of the core particles wherein the slurry pH at the end of the deposition is about 9 or less.

The core particles may be obtained from commercial sources or they may be synthesized by techniques known in the art for the desired core material. The core particles are preferably thoroughly dispersed in an aqueous medium prior to formation of the siliceous oxide coating thereon. Most preferably, the cores are synthesized via precipitation in an aqueous medium and are maintained in contact with an aqueous medium from the moment of their precipitation through the deposition of the silica coating thereon.

For magnetite, the crystals are preferably prepared by an aqueous precipitation process wherein an aqueous solution of $FeCl_2$ (e.g. about 2.5–4 wt. %) and $FeCl_3$ (e.g. about 1–3 wt. %) is formed. The ratio of Fe(II) to Fe(III) may be varied via the relative proportions of the iron chlorides to affect the ratio of iron oxides in the final product. In general, the Fe(II) to Fe(III) ratio is about 1. Under strong agitation, a base such as ammonium hydroxide (preferably as a 14 wt. % $NH_4OH$ aqueous solution) is then rapidly added to the solution at ambient temperature to raise the pH to about 8–10, more preferably about 8.5, whereby microcrystalline magnetite is precipitated. The precipitate slurry is then settled, decanted, and reslurried with water to remove excess ammonium and chloride ions. The settling, decanting and washing steps may be repeated to reduce the level of undesired ions. If desired, centrifugation may be used in place of the settling and decantation steps to accelerate the overall process. Drying of the precipitate prior to formation of the silica coating is preferably avoided.

As noted above, it may be possible to form one or more intermediate layers of a diverse non-siliceous oxide material on the surface of the superparamagnetic or low Curie Temperature material. For example, the surface of the core may be subjected to a mildly oxidizing environment to produce a surface region of slightly higher oxygen content. Most preferably, all intermediate layers are avoided such that the siliceous oxide coating directly contacts the surface of the superparamagnetic or low Curie Temperature material.

For deposition of the siliceous oxide coating, the core particles or core particle slurry is preferably dispersed in water (preferably deionized water). The concentration of particles in the resulting slurry may be varied, but it is preferably about 50 to 100 parts by weight of core particles per 1000 parts by weight of water. Agitation is preferably used to ensure a thorough dispersion of the core particles. Agitation method may range from simply stirring to sonicating (i.e. using ultrasound) or combinations of methods. The slurry is also preferably heated to about 60–95° C. and maintained at such elevated temperature throughout the deposition process.

To deposit the siliceous oxide on the core particles, a siliceous oxide source (preferably sodium silicate) and an acid (preferably a mineral acid such as hydrochloric acid or sulfuric acid) are then added to the slurry. Preferably, the slurry is maintained under agitation throughout the addition of the siliceous oxide source and the acid. The siliceous oxide source and the acid may be added in various orders of addition. Preferably, either the siliceous oxide source and acid are added simultaneously or the siliceous oxide source is added first followed by the addition of the acid. The total proportions of siliceous oxide source and acid added to the slurry should be such that the end pH of the slurry after all additions have stopped is about 9 or less, more preferably about 6–9, most preferably about 7–8. If desired, one or more aging steps may be inserted into the process at any point during the addition. The addition of silicate and acid is preferably conducted in a manner such that precipitation of homogeneous silica particles is substantially avoided.

In one preferred embodiment, a quantity of aqueous sodium silicate solution (e.g., 10.7 wt. % $SiO_2$ and 3.24 wt.

% $Na_2O$) containing the desired amount of silica to be deposited is added to the initial slurry of core particles slowly, e.g. over a period of at least about 45 minutes, more preferably at least about 60 minutes. An acid solution, such as 1 N HCl (or other mineral acid), is then added to the slurry until a pH of about 6–9 (preferably 7–8) is achieved. The slurry is preferably maintained under agitation at elevated temperature (preferably 60–95° C.) throughout the addition of these materials. After the desired pH reduction is achieved, the acid addition is stopped. Preferably, the slurry is then allowed to age for about 15–60 minutes (preferably about 30 min.) at the same elevated temperature. Preferably agitation is maintained during aging.

After the siliceous oxide coating has been formed on the core particles (e.g., after aging), the slurry is then preferably decanted to remove most of the liquid component. The portion containing the coated particles is then preferably subjected to one or more water washes, each being followed by decantation. If further reduction in the sodium cation level is desired, the precipitate-containing portion may be further treated with one or more washes of a dilute ammonium chloride aqueous solution (e.g., 3 wt. % $NH_4Cl$). The resulting precipitate-containing portion may then preferably be subjected to one or more final water washes. If desired, the resulting particles may then be dried (e.g., in a low temperature oven (<120° C.)), however, it is generally preferred to maintain the resulting product in its wetted state (e.g., as an aqueous slurry).

If desired, the resulting particles may be subjected to a mild oxidizing post-treatment to further inhibit leaching of metals from the core. Any post-treatment preferably does not adversely affect the surface silanol content of the particles nor the magnetic properties of the cores. It should be noted that such post-treatments are generally unnecessary and undesirable from the point of increased manufacturing cost.

In an alternative embodiment, a portion of the aqueous sodium silicate solution is slowly added to the initial core particle slurry until a pH of about 7–9 (preferably about 7.5–8) is achieved. Thereafter, the remainder or the aqueous sodium silicate solution corresponding to the desired amount of silica to be deposited and the mineral acid are added simultaneously to the slurry at a slow rate in quantities such that the slurry pH remains substantially unchanged during the addition. The addition is continued on this basis the desired amount of sodium silicate solution has been added. The slurry is preferably maintained under agitation at elevated temperature (60–95° C.) throughout the addition. Preferably, the slurry is then allowed to age for about 15–60 minutes (preferably about 30 min.) at the same elevated temperature. Preferably agitation is maintained during aging. The resulting coated particles may then be washed and optionally post-treated as indicated above.

The invention is further illustrated by the following examples, it should be understood that the invention is not limited to the specific details of the examples.

EXAMPLE 1A

Preparation of Superparamagnetic Iron Oxide Particles

Portions of $FeCl_3$ and $FeCl_2$ were dissolved in deionized water at ambient temperature to form a solution containing 3.24 wt. % $FeCl_3$ and 1.5 wt. % $FeCl_2$. Under strong agitation, a 14 wt. % $NH_4OH$ aqueous solution was quickly added to the solution until a pH of 8.5 was achieved. As a result of the ammonium hydroxide addition, a fine magnetite precipitate ($Fe_3O_4$) was formed. The precipitate was allowed to settle. The most of the liquid component of the mixture was then removed by decantation. The remaining wet precipitate was then reslurried in deionized water to wash the precipitate. This wash procedure was repeated a total of three times to reduce the level of ammonium and chlorine ions. Drying of the precipitate was avoided.

EXAMPLE 1B

Hydrogen Peroxide Treatment of Superparamagnetic Particles 75 g of the magnetite from Example 1A was reslurried in deionized water to achieve a 7.5 wt. % solids concentration. The resulting slurry was agitated and ultrasonically treated while 600 ml of 3 wt. % $H_2O_2$ solution was added to the slurry. The resulting mixture was maintained in this condition for 60 minutes, and then the magnetite was separated from the solution by decantation while drying of the magnetite was avoided. The magnetite was then subjected to three washes, each using 2000 ml deionized water.

EXAMPLE 2

75 g of wet magnetite particles prepared according to Example 1B (based on the amount of magnetite present) was then reslurried in deionized water to form a slurry having a solids content of about 7.5 wt. %. The slurry was heated to about 90° C. and subjected to moderate agitation and sonication. An aqueous sodium silicate solution (10.7 wt. % $SiO_2$ and 3.24 wt. % $Na_2O$) was added to the slurry at a rate of 5 ml/min for about 43 minutes. During this addition, the sonication was maintained for the first 15 minutes only, but the moderate agitation and 90° C. temperature were maintained throughout the addition. The slurry was allowed to age for ten minutes. Then, additional amounts of the sodium silicate solution were added at 5 ml/min for about 20 minutes while the slurry was maintained under moderate agitation at 90° C. The slurry pH after the silicate addition was about 10. Under moderate agitation at 90° C., 1 N HCl was then added to the slurry at a rate of about 12 ml/min until a pH of about 7.5 was achieved. The slurry was allowed to age under agitation for about 30 minutes at 90° C., and then the particles were allowed to settle.

The liquid component of the settled slurry was decanted off, and the wet particles were then subjected to water washing (2000 ml deionized water) and decantation. The washing/decantation were repeated two additional times. The wet particles remaining after decantation were washed with 450 ml of 3 wt. % $NH_4Cl$ aqueous solution for about 30 minutes followed by a further decantation. The $NH_4Cl$ washing/decantation steps were repeated two additional times and were then followed by three additional series of deionized water washing/decantation steps.

A portion of the resulting wet product was then dried at about 110° C., and the particle size, surface area and pore volume were measured. The median particle size was determined using a Horiba light scattering device. The surface area and pore volume (i.e., ml/g), were determined using nitrogen BET. A portion of the dried product was tested for leachability of core metals using the test method described above. The results are given in Table 1 below. The composition of the resulting material is given in Table 3 below.

EXAMPLE 3

75 g of wet magnetite particles prepared according to Example 1B (based on the amount of magnetite present) was then reslurried in deionized water to form a slurry (pH<7) having a solids content of about 7.5 wt. %. While the slurry was heated to about 90° C. and subjected to moderate agitation and sonication, a minor amount of an aqueous sodium silicate solution (10.7 wt. % $SiO_2$ and 3.24 wt. % $Na_2O$) was added at a rate of 5 ml/min until a slurry pH of about 7.7 was achieved. Then, both sodium silicate solution and 1N HCl were added to the slurry simultaneously for about 43 minutes. The rate of HCl addition was adjusted to maintain the pH at 7.7 given a 5 ml/min addition rate for the sodium silicate. During this addition, the sonication was maintained for the first 15 minutes only, but the moderate agitation and 90° C. temperature were maintained throughout the addition. The slurry was allowed to age for ten minutes. Then, additional amounts of the sodium silicate solution (5 ml/min) and HCl were simultaneously added for about 20 minutes while the slurry was maintained under moderate agitation at 90° C. and pH=7.7. The slurry was allowed to age for about 30 minutes at 90° C. under agitation, and then the particles were allowed to settle.

The particles were then subjected to the same washing and testing procedures as described in Example 2 above. The results are reported in Table 1 below. The composition of the resulting material is given in Table 3 below.

TABLE 1

| Example | Surface area (m²/g) | Pore volume (<600Å diameter) (ml/g) | Pore volume (>600Å diameter) (ml/g) | Median particle size (μm) | Iron leach (ppm) |
|---|---|---|---|---|---|
| 2 | 49 | 0.160 | 0.257 | 5.5 | 2.0 |
| 3 | 35 | 0.124 | 0.106 | 8.1 | 3.4 |

EXAMPLE 4

125 g of wet magnetite particles prepared according to Example 1B (based on the amount of magnetite present) was then reslurried in deionized water to form a slurry having a solids content of about 7.5 wt. %. The slurry was heated to about 90° C. and subjected to moderate agitation and sonication. An aqueous sodium silicate solution (10.7 wt. % $SiO_2$ and 3.24 wt. % $Na_2O$) was added to the slurry at a rate of 8.33 ml/min for about 43 minutes. During this addition, the sonication was maintained for the first 15 minutes only, but the moderate agitation and 90° C. temperature were maintained throughout the addition. The slurry was allowed to age for ten minutes. Then, additional amounts of the sodium silicate solution were added at 8.33 ml/min for about 20 minutes while the slurry was maintained under moderate agitation at 90° C. The slurry pH after the silicate addition was about 10. Under moderate agitation at 90° C., 1N HCl was then added to the slurry at a rate of about 20 ml/min until a pH of about 7.5 was achieved. The slurry was then allowed to age under agitation for about 30 minutes at 90° C., and then the particles were allowed to settle.

The particles were then subjected to the same washing and testing procedures as described in Example 2 above. The undried particles were also tested for magnetic separability using the procedure described above. These results are given in Table 2 below. The composition of the resulting material is given in Table 3 below.

EXAMPLE 5

An additional sample was prepared following the same procedure as in Example 4 except that the magnetite particles were prepared according to Example 1A and that the ten minute aging step during the sodium silicate addition was eliminated.

The particles were tested as in Example 4 above. These results are given in Table 2 below. The composition of the resulting material is given in Table 3 below.

EXAMPLE 6

An additional sample was prepared following the same procedure as in Example 2 except that the amount of magnetite particles used was 550 g. The initial slurry volume and the addition rates of sodium silicate and HCl were scaled up in proportion to the increased amount of magnetite used.

The particles were tested as in Example 4 above. These results are given in Table 2 below. The composition of the resulting material is given in Table 3 below. Example 7

125 g of wet magnetite particles prepared according to Example 1A (based on the amount of magnetite present) was then reslurried in deionized water to form a slurry having a solids content of about 7.5 wt. %. The slurry was heated to about 90° C. and subjected to moderate agitation and sonication. An aqueous sodium silicate solution (10.7 wt. % $SiO_2$ and 3.24 wt. % $Na_2O$) was added to the slurry at a rate of 8.4 ml/min for about 95 minutes. During this addition, the sonication was maintained for the first 15 minutes only, but the moderate agitation and 90° C. temperature were maintained throughout the addition. Under moderate agitation at 90° C., 1N HCl was then added to the slurry at a rate of about 20 ml/min until a pH of about 7.5 was achieved. The slurry was then allowed to age under agitation for about 30 minutes at 90° C., and then the particles were allowed to settle.

The particles were then subjected to the same washing and testing procedures as described in Example 4 above. These results are given in Table 2 below. The composition of the resulting material is given in Table 3 below.

EXAMPLE 8

37.5 g of wet magnetite particles prepared according to Example 1A (based on the amount of magnetite present) was reslurried in deionized water to form a slurry having a solids content of about 7.5 wt. %. The slurry was heated to about 90° C. and subjected to moderate agitation and sonication. An aqueous sodium silicate solution (10.7 wt. % $SiO_2$ and 3.24 wt. % $Na_2O$) was added to the slurry at a rate of 5 ml/min for about 43 minutes. During this addition, the sonication, the moderate agitation and 900° C. temperature were maintained. The slurry was allowed to age for ten minutes. Then, additional amounts of the sodium silicate solution were added at 5 ml/min for about 213 minutes while the slurry was maintained under moderate agitation at 90° C. Sonication was maintained for all but the last 20 minutes of the addition. Under moderate agitation at 90° C., 1N HCl was then added to the slurry at a rate of about 12 ml/min until a pH of about 7.5 was achieved. The slurry was then allowed to age under agitation for about 30 minutes at 90° C., and then the particles were allowed to settle.

The particles were then subjected to the same washing and testing procedures as described in Example 4 above. These results are given in Table 2 The composition of the resulting material is given in Table 3 below.

TABLE 2

| Example | Surface area (m²/g) | Pore volume (<600 Å diameter) (ml/g) | Pore volume (>600 Å diameter) (ml/g) | Median particle size (µm) | Iron leach (ppm) | % transmission after 40 sec. | % transmission after 600 sec. |
|---|---|---|---|---|---|---|---|
| 4 | 55 | 0.181 | 0.163 | 5.3 | 2.8 | 87.7 | 98.3 |
| 5 | 48 | 0.147 | 0.110 | 5.6 | 3.3 | 96.7 | 100 |
| 6 | 56 | 0.188 | 0.142 | 8.0 | 3.7 | 89.9 | 100 |
| 7 | 47 | 0.145 | 0.105 | 6.5 | 2.0 | 99.5 | 100 |
| 8 | 6 | 0.020 | 0.017 | 4.7 | 0.7 | 79.2 | 99.4 |

Particle Composition

From chemical analysis of the materials resulting from the above examples 2–7 compositions are given in Table 3 below as weight percent (dry, oxide basis).

TABLE 3

| Example | $SiO_2$ | $Fe_3O_4$ | $Na_2O$ |
|---|---|---|---|
| 2 | 39.1 | 59.7 | 0.19 |
| 3 | 43.1 | 55.2 | 0.11 |
| 4 | 45.6 | 53.1 | 0.16 |
| 5 | 41.6 | 56.1 | 0.12 |
| 6 | 40.6 | 58.0 | 0.10 |
| 7 | 51.3 | 46.5 | 0.15 |
| 8 | 83.6 | 13.6 | 0.25 |

What is claimed is:

1. A particulate adsorbent comprising particles which consist essentially of:
   (a) at least one core consisting essentially of a transition metal-containing component selected from the group consisting of superparamagnetic materials, low Curie Temperature materials, and mixtures thereof, and
   (b) a siliceous oxide coating on the surface of said core(s), wherein said coating covers the entire surface of said core(s) such that said adsorbent particles have a transition metal leach value when present as 0.33 g dried adsorbent particles in 20 ml of 1N hydrochloric acid aqueous solution for 15 minutes of less than about 50 ppm metal based on the weight of said solution.

2. The adsorbent of claim 1 wherein said transition metal is selected from Group VIII transition metals and mixtures thereof.

3. The adsorbent of claim 2 wherein said transition metal-containing component is selected from the group consisting of iron, iron oxides, and mixtures thereof.

4. The adsorbent of claim 3 wherein said transition metal-containing component consists essentially of magnetite.

5. The adsorbent of claim 1 wherein said siliceous oxide coating contains hydroxyl groups on its outer surface.

6. The adsorbent of claim 5 wherein said siliceous oxide coating containing hydroxyl groups on its outer surface consists essentially of silica.

7. The adsorbent of claim 1 wherein said siliceous oxide coating contains externally accessible porosity.

8. The adsorbent of claim 7 wherein said particles contain at least about 0.2 ml/g pore volume measured by nitrogen BET method based on the total dry weight of said particles.

9. The adsorbent of claim 8 wherein said particles contain at least about 0.2 ml/g porosity in pores having a diameter of 60 nm or greater as measured by nitrogen BET method.

10. The adsorbent of claim 1 wherein said particles have a surface area of at least about 30 m²/g measured by nitrogen BET method based on the total dry weight of said particles.

11. The adsorbent of claim 1 wherein said core forms at least about 50 wt. % of said particles based on the combined dry basis weight of said core and said oxide coating.

12. The adsorbent of claim 11 wherein said core forms at least about 60 wt. % of said particles based on the combined dry basis weight of said core and said oxide coating.

13. The adsorbent of claim 1 wherein said core comprises one or more crystals having a crystal size of about 100 nm or less.

14. The adsorbent of claim 13 wherein said crystal(s) have an average crystal size of about 60 nm or less.

15. The adsorbent of claim 1 wherein said adsorbent particles have an average particle size of about 1–15 µm.

16. The adsorbent of claim 15 wherein said adsorbent particles have an average particle size of about 3–10 µm.

17. The adsorbent of claim 1 wherein said core is a superparamagnetic material at room temperature.

18. The adsorbent of claim 17 wherein said superparamagnetic material has a remanent magnetism level of about 10 emu/g or less.

19. The adsorbent of claim 17 wherein said superparamagnetic material has a remnant magnetism level of about 2 emu/g or less.

20. The adsorbent of claim 1 wherein said core(s) consists essentially of a material having a Curie Temperature of about −50° C. to 100° C.

* * * * *